United States Patent [19] [11] 4,129,740
Zengel et al. [45] Dec. 12, 1978

[54] PROCESS FOR THE PREPARATION OF PARA-NITROSO-DIPHENYLHYDROXYLAMINES

[75] Inventors: Hans Zengel, Kleinwallstadt; Manfred Bergfeld, Erlenbach, both of Germany

[73] Assignee: Akzona Incorporated, Asheville, N.C.

[21] Appl. No.: 873,327

[22] Filed: Jan. 30, 1978

[30] Foreign Application Priority Data

Jan. 31, 1977 [DE] Fed. Rep. of Germany ....... 2703919

[51] Int. Cl.$^2$ ..................... C07C 79/46; C07C 85/24; C07C 101/72
[52] U.S. Cl. ..................................... 560/48; 560/21; 560/45; 560/46; 560/47; 260/571; 260/576
[58] Field of Search ................ 260/576, 571; 560/27, 560/21, 48

[56] References Cited

U.S. PATENT DOCUMENTS 3,933,848   1/1976   Feinstein et al. ............... 260/576 X

FOREIGN PATENT DOCUMENTS 1147237   4/1963   Fed. Rep. of Germany ........... 260/576
2020043  10/1970   Fed. Rep. of Germany ........... 260/576

OTHER PUBLICATIONS

Bamberger et al., "Berichte," vol. 31, pp. 1513-1522, (1898).
Boyer, "J. Org. Chem," vol. 24, p. 2038 (1959).

Primary Examiner—Winston A. Douglas
Assistant Examiner—John Doll
Attorney, Agent, or Firm—Francis W. Young; Robert F. Green

[57] ABSTRACT

An improved process for the preparation of para-nitroso-diphenylhydroxylamines is disclosed. One member of the group consisting of nitrosobenzene, ortho-substituted nitrosobenzenes, meta-substituted nitrosobenzenes, ortho-meta-disubstituted nitrosobenzenes and para-substituted nitrosobenzenes is reacted with one member selected from the group consisting of nitrosobenzene, ortho-substituted nitrosobenzenes, meta-substituted nitrosobenzenes, and ortho-meta-disubstituted nitrosobenzenes, in the presence of an acid catalyst. The improvement comprises utilizing as the acid catalyst an acid selected from the group consisting of aliphatic, cycloaliphatic, and aromatic sulfonic acids, having a $pK_a$ equal to or less than one, perchloric acid, and trifluoroacetic acid, in an amount equal to or greater than 0.5 mol of acid per mol of nitroso reactants, and performing the reaction at a temperature from about −20° C to about 60° C.

8 Claims, No Drawings

PROCESS FOR THE PREPARATION OF PARA-NITROSO-DIPHENYLHYDROXYLAMINES

BACKGROUND OF THE INVENTION

This invention relates to a process for the preparation of certain p-nitroso-diphenylhydroxylamines.

It is known that p-nitroso-diphenylhydroxylamines may be obtained through the dimerizing rearrangement of nitrosobenzenes in concentrated sulphuric acid, E. Bamberger et al., Ber. 31 p. 1513 (1898). As such a process is strongly exothermic, relatively large quantities of concentrated sulphuric acid have been utilized to obtain adequate mixing and dissipation of heat. To separate the reaction product, ice, or water, must be added to the mixture. Large quantities of dilute sulphuric acid accumulating thereby are neutralized and subsequently discharged as waste water, as reclamation of the sulphuric acid, is not economically justifiable, especially due to its contamination with nitrogen-containing organic materials. As a consequence, the foregoing process is not suitable for industrial-scale preparation of p-nitroso-hydroxylamines.

German patent application disclosure No. 2,020,043 teaches that the dimerizing rearrangement of the nitrosobenzenes may be performed with a sulphuric acid of at least 50% by weight, preferably at least 75% by weight, in the presence of an organic liquid, such as an aliphatic hydrocarbon, a halogen hydrocarbon, or an aromatic nitro compound, at a temperature of 5° to 50° C. Since, at the elevated temperatures, the reaction product decmposes very quickly in the strongly acidic solution, it is necessary to remove the heat of reaction quickly, and this is accomplished by the organic liquid. However, in such a process, as well, sulphuric acid is utilized in a large excess, namely, up to 10 times, preferably 2.5 to 6.5 times the molar quantity of nitrosobenzene. Thus, the previously discussed disadvantages of the process according to Bamberger et al. are also encountered in the process of the German patent application. Aside from the foregoing, the quality of the reaction product is not totally acceptable. In addition to products sulfonated in the nucleus, the products also contain considerable quantities of other constituents. When stoichiometric quantities of sulphuric acid are utilized, the p-nitroso-diphenylhydroxylamine is obtained in the form of its sulfate, as a tough, dark mass, technically hard to handle, which, in addition to products sulfonated in the nucleus, also contains substantial quantities of tar.

In German Pat. No. 1,147,237, a process is disclosed which utilizes hydrogen fluoride as a dimerizing agent, rather than concentrated sulphuric acid. The rearrangement takes place at a temperature between $-20°$ C. and 50° C., if necessary in the presence of an inert organic solvent, K. Wiechert et al., Z. Chem. 15 (1975), p. 21. In the foregoing process, as well, the dimerizing agent is utilized in great excess, because the hydrogen fluoride serves not only as a catalyst, but also as a solvent. When the hydrogen fluoride is utilized in stoichiometric quantities, one obtains the yield of only 25%, of theoretical. In addition, the product is contaminated with products fluorinated in the nucleus. After the reaction, the hydrogen fluoride may be distilled off under a vacuum and may be recirculated. However, hydrogen fluoride has a low boiling point, an extremely penetrating odor, and, when inhaled, its vapors are very poisonous. Aside from the foregoing, the desired product is obtained as a viscous mass, which is still contaminated with 10 to 20% of adhering hydrogen fluoride. It is practically impossible to reclaim the adhering hydrogen fluoride, since, under the conditions required to accomplish the same, the p-nitroso-diphenylhydroxylammonium fluorides decompose into a brownish-black mass. Thus, the wash water is also contaminated with hydrogen fluoride. Furthermore, there are corrosion problems associated with such a process. Execution of the process therefore requires high expenditures for equipment, so that such a process, as well, is not very suitable for industrial-scale preparation of p-nitroso-diphenylhydroxylamines.

Furthermore, it is known that in the treatment of nitrosobenzene with peroxytrifluoroacetic acid, p-nitrosodiphenylhydroxylamine will be formed in addition to nitrobenzene, J. H. Boyer, J. Org. Chem. 24 (1959), p. 2038. Thus, the peroxytrifluoroacetic acid, on the one hand, oxidizes the nitrosobenzene to nitrobenzene, and on the other hand, it catalyzes the dimerization of the nitrosobenzene to p-nitrosodiphenylhydroxylamine. At higher temperatures it favors the formation of nitrobenzene, and at lower temperatures, that of p-nitroso-diphenylhydroxylamine. In the most favorable case, one obtains 35% of theoretical, of p-nitroso-diphenylhydroxylamine, and thus such a process is not very selective and likewise is not very well suited for the industrial-scale preparation of p-nitroso-diphenylhydroxylamines.

The primary object of the present invention is therefore to provide a process for the preparation of p-nitroso-diphenylhydroxylamines, which may be utilized in an industrialscale operation.

SUMMARY OF THE INVENTION

The foregoing object, and others, are achieved by the present invention which provides an improved process for the preparation of p-nitroso-diphenylhydroxylamines. In the process one member selected from the group consisting of nitrosobenzene, ortho-substituted nitrosobenzenes, meta-substituted nitrosobenzenes, ortho-meta-disubstituted nitrosobenzenes, and para-substituted nitrosobenzenes is reacted with one member selected from the group consisting of nitrosobenzenes, orthosubstituted nitrosobenzenes, meta-substituted nitrosobenzenes, and ortho-meta-disubstituted nitrosobenzenes, in the presence of an acid catalyst. The improvement comprises utilizing as the acid catalyst an acid selected from the group consisting of aliphatic, cycloaliphatic, and aromatic sulfonic acids, having a $pK_a$ equal to or less than 1, perchloric acid, and trifluoroacetic acid, in an amount equal to or greater than 0.5 mol of acid per mol of nitroso reactants, and performing the reaction at a temperature from about $-20°$ C. to 60° C.

DESCRIPTION OF THE PREFERRED EMBODIMENTS

The process pursuant to the present invention is especially suitable for the preparation of p-nitroso-diphenylhydroxylamine by means of the dimerizing rearrangement of nitrosobenzene. It is, however, likewise suitable for the preparation of asymmetrically substituted p-nitroso-diphenylhydroxylamines, which are obtained by the dimerizing rearrangement of ortho- or meta-substituted nitrosobenzenes, or through reaction of a para-substituted nitrosobenzene with a nitrosobenzene unsubstituted in the para position. As initial material one may utilize all nitroso compounds of the benzene series, the substituents of which behave in an inert manner with regard to the catalyst. Examples thereof are nitro, alkoxy, halogen alkyl, alkyl, and carboalkoxy groups. The nitroso compounds may be singly substituted, as well as multiple substituted. Thus, the term "substituted" when used throughout this application and in the appended claims means "substituted with any substituent which behaves in an inert manner with regard to catalysts utilized in the process of the present invention."

The ortho-substituted nitrosobenzenes used in the practice of the present process contain at least one orthosubstituent, but in addition thereto, may contain a second substituent in the other ortho-position. The meta-substituted nitrosobenzenes used in the practice of the present invention contain at least one ortho-substituent, but in addition thereto, may contain a second substituent in the other meta-position. The para-substituted nitrosobenzenes used in the practice of the present invention may contain a second substituent in either of the ortho- or meta-positions, in addition to the substituent in the para-position. The ortho-meta-disubstituted nitrosobenzenes contain a substituent in either of the ortho-positions and a substituent in either of the para-positions.

The preferable reactants utilized in the practice of the process of the present invention include: o-nitrosotoluene, o-chloronitrosobenzene, m-chloronitrosobenzene, o-methoxynitrosobenzene, o-nitronitrosobenzene, m-trifluoromethylnitrosobenzene, 2,6-dichloronitrosobenzene, 2,6-dimethylnitrosobenzene, m-fluoronitrosobenzene, o-methylnitrosobenzene, 2,5-dichloronitrosobenzene, m-nitronitrosobenzene, and 2-nitrosobenzoic acid methylester. Of course, mixtures of one or more of the referenced materials may be utilized in the practice of the process of the present invention.

The referenced acids are excellent catalysts and, with respect to their effectiveness and selectivity, surpass all acids heretofore utilized in the preparation of p-nitroso-diphenylhydroxylamines. Because of the ease of handling of the acids, their lower price, their ease of separability and their reclaimability, the sulfonic acid, in particular, are especially well suited as catalysts. Preferred sulfonic acids are methane, trifluoromethane, ethane, cyclohexane, benzene and p-toluene sulfonic acid, but other sulfonic acids with a $pK_a$ equal to or less than 1, such as xylene and cresol sulfonic acid, as well as industrial-type sulfonic acid mixtures may be utilized.

The quantity of catalyst to be used depends only within certain limitations upon the type of acid. The general range for the quantity of catalyst is from about 0.5 to about 10 mol, per mol of nitroso compound. However, a special advantage of the catalysts pursuant to the present invention consists in the fact that they can be utilized in smaller quantities than the customary acids, namely, preferably, in quantities from about 0.8 to about 2 mol per mol of nitroso compound. Such a characteristic is not only economically advantageous, but also substantially facilitates processing of the reaction mixture. However, in order to obtain high yield, it is desirable to use the catalyst at least in a stoichiometric ratio, i.e., in quantities of at least 1 mol per mol of nitroso compound. The use of less catalyst, in accordance with the foregoing amounts, is operable, but the especially desirous high yields are only obtained if the catalyst is utilized in a quantity of at least 1 mol per mol nitroso compound.

The process pursuant to the present invention may be carried out in the presence, as well as in the absence, of an organic solvent. In both cases, the reaction will proceed with a high yield of selectivity. However, use of an organic solvent offers a number of advantages in the processing of the reaction mixture.

When utilizing an organic solvent, it is not absolutely necessary to work in a homogeneous phase, but the nitroso compound, as well as the catalyst, should be at least partly soluble in the solvent. It is also desirable, that the forming salt of the p-nitroso-diphenylhydroxylamine be soluble in the solvent, since under such conditions the reaction product can be obtained in a very pure form. Suitable solvents include aliphatic, cycloaliphatic, and aromatic hydrocarbons, which may carry one or several alkyl, halogen and/or nitro groups. The solvents nitromethane, nitrobenzene, methylene chloride, chloroform, 1,2-dichloroethane, 1,1,1-trichloromethane, and 1,1,2,2-tetrachloroethane are preferred.

Rather than utilizing an organic solvent, excess dimerizing agent may also serve as reaction medium. In such instance, the sulfonic, perchloric, or trifluoroacetic acid is utilized in quantities of about 5 to about 50 mol per mol of the nitroso compounds.

The reaction of the present invention may be carried out at a temperature from about $-20°$ C. to about $60°$ C., preferably between about $0°$ C. and about $45°$ C. The reaction is strongly exothermic, and careful cooling of the reaction mixture is therefore necessary. This applies in particular, when the reaction is performed in the absence of a solvent.

The reaction time depends upon the type of nitrosobenzene utilized, the presence of absence of a solvent, perhaps upon the quantity of solvent, upon the type and quantity of catalyst, as well as upon the reaction temperature. It is influenced most strongly by the concentration of the nitrosobenzene in the reaction mixture and by the quantity of catalyst. The reaction time is shortened by an increase in nitrosobenzene concentration and an increase in catalyst quantity. Preferably, one commences with solutions of from about 5 to about 30%, by weight, of the nitroso compound in the organic solvent, in which case the duration of the reaction amounts to from about 30 seconds to about 2 hours. Very short reaction times of 30 seconds to a few minutes will result from the use of nitrosobenzene solutions of from about 15 to about 30%, by weight, and a nitrosobenzene/catalyst ratio of at least 1:1.5. Under such conditions, 98% of the initial material is dimerized after about 45 seconds, in the case of nitrosobenzene/methane sulfonic acid. Among other things, short reaction times offer the advantage that the reaction product is obtained with high purity.

Depending upon the type of catalyst, the influence of water on the effectiveness of the present process varies greatly. For example, in the case of nitrosobenzene, the reaction can be carried out with high yield in nitrobenzene or chloroform, utilizing commercial grade, 70% by weight, perchloric acid. On the other hand, for example, in the case of p-toluene sulfonic acid, the high yield of p-nitroso-diphenylhydroxylamine obtainable when anhydrous acid is utilized declines very much if, instead of the latter, use is made of a 93.75% acid (p-toluene sulfonic acid monohydrate). It is therefore advisable to use the acids in a form that is, if possible, anhydrous, or cotains a low water content. The water content of the catalyst that can be tolerated with a view toward a good yield therefore varies greatly. It can be easily determined from case to case by means of simple tests.

Suitably, the process pursuant to the present invention is carried in such a manner that one commences with a solution, or a suspension, of the nitroso compound or compounds in the organic solvent, to which the catalyst is added in portions, with vigorous stirring, and with cooling. It is advantageous to perform the reaction in a low-boiling solvent, such as methylene chloride, with refluxing, in which case the heat of reaction is removed in a simple manner by evaporation cooling. Thus, depending upon the type of solvent and type of catalyst, a clear solution of a salt of p-nitroso-diphenylhydroxylamine will be quickly formed, or less quickly, with the catalyst acid. After termination of the addition, the reaction mixture is stirred briefly in order to complete the reaction. Subsequently, the reaction solution is diluted with water, whereby the salt decomposes, the p-nitroso-diphenylhydroxylamine precipitates, and the solvent evaporates. The precipitate is washed until neutral and finally dried. Usually, a second fraction of the reaction product can be extracted from the filtrate.

If an organic solvent is absent, it is suitable to start with the catalyst and to add the nitroso compound(s) in portions with cooling and vigorous agitation. Solid sulfonic acids are first melted. After removal of the excess catalyst, it is advantageous to pour the obtained reaction mixtures into ice water and to process them in the manner described above.

The catalyst acid can be reclaimed in a simple manner through concentration of the mother liquor, whereupon it may be utilized again. When use is made of the preferred processing conditions, the process pursuant to the present invention proceeds with practically quantitative yields. A form of execution of the process pursuant to the invention which is especially well suited for the industrial preparation of p-nitroso-diphenylhydroxylamine consists in executing the dimerization with an approximately 25%, by weight, solution of nitrosobenzene and methane sulfonic acid in refluxing methylene chloride. Under such conditions, depending upon the quantity of acid utilized, the reaction is practically quantitative after only 1 to 15 minutes.

Because of the attainable short reaction times, the process pursuant to the present invention is especially well suited for the continuous preparation of p-nitroso-diphenylhydroxylamines. Thus, it is, for example, possible to mix the solution of nitrosobenzene(s) in an organic solvent thoroughly with the catalyst by means of a mixing nozzle and to complete the reaction subsequently in the course of about 1 to about 5 minutes.

In the process pursuant to the present invention, the nitroso-phenylhydroxylamines accumulate with a high degree of purity. If required, they may be purified further in a known manner, such as by recrystallization or reprecipitation, by first dissolving the product in an aqueous alkali or alkaline earth hydroxide, or in sodium sulfite, whereupon it may be precipitated again by the addition of a mineral acid.

The nitroso-diphenylhydroxylamines are valuable compounds themselves, and they may be processed further, for example, into antioxidants, anti-ozone agents and dyestuffs.

The following non-limiting Examples will further exemplify the process of the present invention.

EXAMPLE I

In a 4 liter three-neck flask, 475 g (4.4 mol) of nitrosobenzene were suspended in 2 liters of methylene chloride by stirring vigorously with a KPG agitator. Due to partial solution of the nitrosobenzene in methylene chloride, the latter is cooled from 20° C. to 10° C. In the course of 15 minutes, 633 g (6.58 mol) of methane sulfonic acid were now added drop by drop to the dark green suspension with vigorous stirring. As soon as the first drops of methane sulfonic acid were added, the dark green color of the nitrosobenzene disappeared and a deep red solution of nitroso-diphenylhydroxylamine methane sulfonate was formed. Cooling was necessary, since the reaction is strongly exothermic. The internal temperature was held to 25° C. to 28° C. After termination of the addition of methane sulfonic acid, stirring was continued for 5 minutes at 30° C. and the formed clear red solution was sprayed into 1700 ml of water at 35° C. in a rotation evaporator under a water-jet vacuum, whereby the salt decomposed to nitroso-diphenylhydroxylamine, and the methylene chloride was distilled off at the same time. In this manner of processing, the p-nitroso-diphenylhydroxylamine accrued as a fine, yellow powder, which was easy to filter off from the dilute methane sulfonic acid. After it had been washed until neutral with a little ice water, it was dried at 60° C./40 Torr. Yield: 445.5 g = 95% of theoretical. Melting point: 143°–144° C.

EXAMPLE II 51 g nitrosobenzene (0.476 mol) were suspended in 200 ml methylene chloride, whereupon 78.5 g (0.71 mol) ethane sulfonic acid were added thereto at 2° C. with vigorous stirring, analogous to Example I. The ethane sulfonic acid was thereby added drop by drop at such a velocity, that the internal temperature did not exceed 30° C. After 15 minutes, all of the sulfonic acid had been added and a clear red solution had been formed from the at first green suspension of the nitrosobenzene in methylene chloride. Processing was carried out analogous to Example I and 49.5 g of p-nitroso-diphenylhydroxylamine = 96% of the theory were obtained through filtration after drying.

An additional 1.75 g (3.4% of the theory) of p-nitrosodiphenylhydroxylamine were obtained from the filtrate (dilute methane sulfonic acid) by means of extraction with methylene chloride for 5 hours. The total yield therefore was 99.1% of theoretical.

EXAMPLE III 28.1 g of nitrosobenzene (0.262 mol) were dissolved in 200 ml methylene chloride at room temperature, whereupon 63.2 g (0.385 mol) of cyclohexane sulfonic acid, diluted with 50 ml methylene chloride were added thereto at 5° C. to 20° C. with vigorous stirring and external cooling. After termination of the drop by drop addition, stirring was continued for 1 hour at 20° C. for a completion of the reaction, whereupon the clear, red solution was processed analogous to Example I. After filtration and drying the p-nitroso-diphenylhydroxylamine was obtained with a yield of 26.3 g = 93.5% of the theory, in the form of a light brown, fine powder. The reaction of nitrosobenzene was quantitative.

EXAMPLE IV 20.5 g nitrosobenzene (0.191 mol) were dissolved in 330 ml of chloroform in a 1 liter three-neck flask equipped with dropping funnel, KPG stirrer and reflux cooler, whereupon the clear, green solution was cooled down to 0° C. to 2° C. Now, 60.5 g crystalline benzene sulfonic acid (0.382 mol) ("for purposes of synthesis" = 97% + 3% water) were added by portions in the course of 5 minutes. External cooling was used to make sure that the internal temperature would not exceed 25° C. Since benzene sulfonic acid dissolves only moderately well in chloroform, the conversion proceeds heterogeneously and the benzene sufonic acid will dissolve completely only in the course of the reaction, since the forming benzene sulfonic acid salt of p-nitrosodiphenylhydroxylamine dissolves well in chloroform. After 1 hour the nitrosobenzene had been converted quantitatively and the chloroform was now distilled off under a vacuum at 10° C. A viscous mass remained behind which, in addition to excess benzene sulfonic acid, as well as the benzene sulfonic salt of p-nitrosodiphenylhydroxylamine, also contained traces of chloroform. This mixture was now dissolved in 150 ml of methanol at room temperature and the clear, dark red solution, while being vigorously stirred was poured onto 500 ml of ice water. A light brown precipitate formed immediately, which was filtered off, washed until neutral with ice water, and dried in a vacuum at 40° C. The uield was 19.8 g = 96.8% of theoretical. The purity was determined by means of elementary analysis, as well as potentiometric titration with NaOH against the sodium slat of diphenylhydroxylamine.

EXAMPLE V 5.1 L g of nitrosobenzene (47.5 mmol) were suspended in 20 ml methylene chloride at 0° C. in a 50 ml two-necked flask with vigorous agitation by means of a magnetic stirrer. To this suspension, 12.15 g (70.56 mmol) of anhydrous p-toluene sulfonic acid (prepared from p-toluene sulfonic acid monohydrate by heating to 250° C./1 Torr) in the form of a solution in 15 ml methylene chloride were added drop by drop within 5 minutes, whereby the internal temperature rose to 40° C. After termination of the addition, stirring was continued for one-half hour in order to complete the reaction. Processing was continued by spraying into warm water of 30° C.–40° C. under a vacuum, analogous to Example I. As explained there in detail, this was followed by filtering, washing until neutral and drying under a vacuum at 50° C. The yield of p-nitroso-diphenylhydroxylamine was 4.78 g, i.e., 93.8% of theoretical.

EXAMPLE VI

Analogous to Example V, 5.007 g (46.75 mmol) of nitrosobenzene were dissolved in 30 ml of methylene chloride and, after cooling to 2° C., 10.52 g (70.1 mmol) of trifluoromethane sulfonic acid (98%) were added thereto drop by drop within 5 minutes. Thereby, the reaction temperature rose to 45° C. To complete the reaction, stirring was continued for one-half hour at room temperature, whereupon the dark reddish borwn suspension was sprayed into warm water under a vacuum, as already described in Example I. After washing until neutral and drying, 4.8 g (95% of the theory) of p-nitroso-diphenylhydroxylamine were obtained as a light brown powder. After extraction for 5 hours with methylene chloride, it was possible to obtain an additional 0.3 g of p-nitroso-diphenylhydroxylamine from the filtrate as a brown powder, so that a quantitative yield was obtained with 100% conversion.

EXAMPLE VII 20.5 g (0.191 mol) of nitrosobenzene were dissolved in 340 ml of chloroform and 54.7 g (0.381 mol) of 70% perchloric acid added thereto, drop by drop, at room temperature in the course of 10 minutes with vigorous stirring. Two phases were formed already when the first drops of perchloric acid were added, namely, a light red chloroform phase and a dark reddish brown, aqueous perchloric acid phase. A quantitative conversion therefore requires intensive mixing. This was achieved by stirring vigorously for 1 hour at 20° C. After it was no longer possible to detect any nitrosobenzene, the chloroform was distilled off under a vacuum and the dark reddish brown, viscous residue dissolved in 100 ml of methanol. A clean solution has been formed which was poured onto 500 ml of ice water. 17.2 g (= 84% of theoretical) of p-nitroso-diphenylhydroxylamine were obtained thereby in the form of a dark brown powder. Purification is possible by conversion to the Na salt with dilute soda lye and subsequent precipitation with dilute mineral acids at pH = 5–6.

EXAMPLE VIII 5.33 g of nitrosobenzene (50 mmol) were dissolved in 37 g nitrobenzene, cooled to 10° C. and then 11.36 g (7.62 mmol) of trifluoroacetic acid were added thereto in the course of 10 minutes. When the trifluoroacetic acid was added, the dark green solution became reddish brown and the temperature rose to 30° C. After stirring had been continued for 30 minutes, the excess trifluoroacetic acid was distilled off under a vacuum at room temperature. This was only partly successful, and a viscous, brown product remained behind. Further processing was performed as described in Example VII, by dissolving the syrupy mass in methanol and precipitating the p-nitroso-diphenylhydroxylamine by pouring onto 100 ml of ice water. 3.5 g (= 65.6% of theoretical) of p-nitroso-diphenylhydroxylamine were obtained as a brown powder after washing until neutral and drying, with 96% conversion of the nitrosobenzene.

EXAMPLE IX 60 ml of methane sulfonic acid (98%, corresponding to 0.922 mol) were put in a 100 ml two-necked flask and 30.8 g (0.288 mol) of nitrosobenzene added thereto by portions at 20° C. The strongly exothermic reaction required vigorous stirring and, in addition, external cooling was needed to make sure that the internal temperature would not exceed 40° C. The entire nitrosobenzene had been added with 45 minutes and a dark red, viscous solution had been formed. To complete the reaction, stirring was continued for 1 hour at room temperature and subsequently the p-nitroso-diphenylhydroxylamine precipitated by pouring the reaction mixture into 1 liter of ice water. After washing until neutral and drying under a vacuum, 26.9 g (= 87.4% of theoretical of p-nitroso-diphenylhydroxylamine were obtained in the form of a dark brown powder. Extraction of the aqueous filtrate for 4 hours with methylene chloride permitted isolating another 2.75 g (= 8.92%), so that the total yield of crude p-nitroso-diphenylhydroxylamine amounted to 96.4% of theoretical.

EXAMPLE X 50 ml of trifluoroacetic acid (about 0.65 mol) in a round-bottomed flask were cooled to 0° C. with vigorous stirring and 5.35 g (50 mmol) of nitrosobenzene added thereto by portions in the course of 15 minutes. The addition of the nitrosobenzene had been chosen in such a way, that the internal temperature would not exceed 18° C. After termination of the addition, stirring was continued for 20 minutes at room temperature. Subsequently, as much as possible of the excess trifluoroacetic acid was removed under a vacuum and the viscous residue mixed with ice water. Filtration and drying resulted in a dark brown raw material, from which it was possible to obtain 4.65 g (21.7 mmol = 87% of theoretical) of p-nitroso-diphenylhydroxylamine by recrystallization from methylene chloride.

EXAMPLE XI 19.44 g (0.113 mol) of anhydrous p-toluene sulfonic acid were melted to a clear, syrupy liquid in a 100 ml round-bottomed flask and, in the course of 10 minutes, added by portions to 3.045 g (31.8 mmol) of nitrosobenzene. Subsequently, the reaction was allowed to continue for 1 hour at 45° C. After that, the viscous reaction mixture was poured onto 200 ml of ice water with vigorous stirring. A dark brown, finely crystalline precipitate appeared immediately, from which it was possible to obtain 2.95 g = 86.7% of theoretical of p-nitrosodiphenylhydroxylamine by recrystallization from methylene chloride. Extraction of the methane sulfonic acid filtrate with methylene chloride permitted isolation of another 0.5 g of crude p-nitrosodiphenylhydroxylamine.

EXAMPLE XII

Analogous to Example IX, 8.9 g of methane sulfonic acid (92 mmol) at 20° C. were put in a 100 ml round-bottomed flask, to which 3.08 g (28.75 mmol) of nitrosobenzene, dissolved in 20 ml nitrobenzene, were added by portions in the course of 7 minutes with vigorous stirring, whereby the reaction temperature rose to 35° C. The clear, dark red solution was processed analogous to Example IX, resulting, after recrystallization, in 2.93 g (95.1% of theoretical) of p-nitroso-diphenylhydroxylamine.

EXAMPLE XIII 19.7 g of nitrosobenzene (0.184 mol) were dissolved in 300 ml of 1,1,2,2-tetrachloroethane with vigorous stirring at 15° C., whereupon 26.5 g (0.276 mol) of methane sulfonic acid were added drop by drop to the dark green solution in the course of 10 minutes. The deeply dark red color of the methane sulfonic acid salt appeared immediately. The reaction temperature was kept below 20° C. by means of external cooling. Stirring was continued for 1 hour at room temperature after all the acid had been added, whereupon the deeply dark red solution was poured onto 500 ml of ice water with vigorous stirring. Since phase separation was bad, the reaction mixture was vigorously shaken five times, every time with 50 ml of 10% soda lye, and the aqueous-alkaline phase separated from the organic phase. Following that, the alkaline aqueous, dark red phase (sodium salt of p-nitroso-diphenylhydroxylamine) was neutralized with dilute hydrochloric acid. This resulted in 18.3 g (= 92.5% of theoretical) of p-nitrosodiphenylhydroxylamine in the form of a fine, yellow powder.

EXAMPLE XIV

In 50 ml of nitromethane were dissolved 6.3 g (59 mmol) of nitrosobenzene at room temperature and then cooled to 10° C. Now, 11.3 g (118 mmol) of methane sulfonic acid were added drop by drop in the course of 5 minutes with vigorous stirring and external cooling (internal temperature not above 22° C.). The dark reddish brown solution was stirred another one-half hour at room temperature to complete the reaction, subsequently decomposed with 100 ml of ice water and, analogous to Example XIII, vigorously shaken several times with dilute soda lye. The aqueous alkaline phase was separated from the organic phase, whereupon, following acidification with dilute hydrochloric acid, 5.6 g (88.9% of theoretical) of p-nitroso-diphenylhydroxylamine were obtained in the form of a fine, yellow powder.

EXAMPLE XV 11.75 g (0.110 mol) of nitrosobenzene were suspended with vigorous stirring in 100 ml of 1,1,1-trichloroethane that had been cooled to 5° C. Subsequently, 11.6 g (120 mmol) of methane sulfonic acid were carefully added drop by drop in the course of 35 minutes, whereby the internal temperature did not exceed 25° C. After addition of the acid had been terminated, stirring was continued for 1 hour at room temperature in order to complete the reaction and then the dark red solution sprayed into a rotation evaporator on 50 ml of water of 50° C. under reduced pressure, whereby the p-nitroso-diphenylhydroxylamine precipitated and the 1,1,1-trichloroethane was removed at the same time. After filtration and drying, 9.3 g (78.5% of theoretical) of p-nitroso-diphenylhydroxylamine were obtained in the form of light brownn, fine crystals.

EXAMPLE XVI

In a 250 ml two-necked flask, equipped with KPG agitator and dropping funnel, 10.09 g (94.2 mmol) of nitrosobenzene were suspended in 150 ml of 1,2-dichloroethane at room temperature. Because of the relatively low solubility of the nitrosobenzene in 1,2-dichloroethane, the reaction was carried out at 50° C. For this purpose, th nitrosobenzene was dissolved in the 1,2-dichloroethane by heating to 60° C., whereupon, after cooling to 30° C., 13.58 g (0.141 mol) of methane sulfonic acid were added at such a rate, that the temperature of the reaction mixture reached between 45° C. and 55° C. Two phases formed, since methane sulfonic acid is also only moderately soluble in 1,2-dichloroethane, so that a successful conversion absolutely requires very thorough mixing. A quantitative conversion had been reached after about 30 minutes and two dark red phases had formed. The upper phase contained most of the solvent, as well as a large part of the methane sulfonic acid salt. The lower phase contained a small quantity of p-nitroso-diphenylhydroxylamine, as well as most of the methane sulfonic acid. Processing was now performed by spraying the reaction mixture into warm water in a rotation evaporator, with simultaneous removal of the 1,2-dichloroethane under a vacuum. After filtration and drying analogous to Example I, it was in this manner possible to obtain 9.66 g (95.7% of theoretical) of p-nitroso-diphenylhydroxylamine in the form of a finely crystalline, brown powder.

EXAMPLE XVII 5.063 g (47.3 mmol) of nitrosobenzene were dissolved in 50 ml of methylene chloride at room temperature and 6.72 g (70 mmol) of 98% methane sulfonic acid added thereto in the course of 1 minute. To complete the reaction, the dark red, clear solution was stirred for another 30 minutes at room temperature and subsequently processed by spraying into warm water under a vacuum and removal of the solvent. Thereby, filtration produced 4.83 g of (= 95.33% of theoretical) of p-nitroso-diphenylhydroxylamine, while another 0.165 g were obtained from the methane sulfonic acid diluted with water to 4% by weight through extraction with methylene chloride. The total yield of p-nitroso-diphenylhydroxylamine was 98% of theoretical. A methane sulfonic acid with a concentration of 98.9% was again prepared from the dilute methane sulfonic acid by distilling off the water (final stage: 130° C./11 Torr.) This acid, without any additional purification, was used for another experiment under otherwise identical conditions. In this case, the yield of p-nitroso-diphenylhydroxylamine was 95.4% of theoretical as a result of filtration and a total of 98.2% of theoretical after filtration and extraction. When the aqueous methane sulfonic acid accumulating in this case was again concentrated to 98% and re-used, the total yield of p-nitroso-diphenylhydroxylamine was 99% of theoretical. In another charge the total yield was 95%. When used again, the yield was 98.8% and finally, in the sixth experiment, 97.5% of theoretical.

EXAMPLE XVIII 4.982 g of 97% ortho-nitrosotoluene (41.12 mmol) were dissolved in 20 ml of methylene chloride at room temperature and 5.93 g of 98% methane sulfonic acid (61.7 mmol = molar ratio of 1:1.5) added thereto in the course of 2 minutes. Stirring was continued for one-half hour at room temperature and subsequently the dark brown, clear solution sprayed into water of 30° C. under a vacuum, whereby the methylene chloride was distilled off simultaneously. By means of filtration, it was possible to obtain 4.85 g = 97% of theoretical, of N-(2-methylphenyl)-N-(3-methyl-4-nitrosophenyl)-hydroxylamine in the form of a light yellow powder.

EXAMPLE XIX 5.0 g (40 mmol) of m-fluoronitrosobenzene were dissolved in 15 ml of methylene chloride (dried over $CaCl_2$) at room temperature and 5.76 g (60 mmol) of methane sulfonic acid added thereto in the course of 5 minutes, whereby cooling was used to make sure that the internal temperature of the reaction vessel would not exceed 25° C. After the entire quantity of methane sulfonic acid had been added, stirring was continued for another 45 minutes at room temperature, to complete the reaction and subsequently the dark red solution sprayed into water of 25° C. under a vacuum, whereby the methylene chloride distilled off at the same time.

By means of filtration it was possible to isolate 1.82 g (72.5% of theoretical) of N-(3-fluorophenyl)-N-(2-fluoro-4-nitrosophenyl)-hydroxylamine in the form of a canary yellow compound. The dimeric compound can be purified by dissolving in $Ca(OH_2)$ and subsequent precipitation of the water-soluble, dark red Ca salt with dilute sulphuric acid, and will then melt at 131° C.–133° C., resulting in a dark red liquid.

EXAMPLE XX 15.2 g (100 mmol) of 2-nitro-nitrosobenzene were added by portions to 60 ml of methane sulfonic acid (98%, corresponding to 0.922 mol) at 10° C. with vigorous stirring, whereby the heat of reaction was removed by cooling. The addition of the nitroso compound was terminated after 15 minutes, whereupon stirring was continued for 1 hour at room temperature to complete the reaction.

The dark red solution was then poured onto 250 g of ice and the precipitate filtered off. After careful washing until neutral with sodium bicarbonate solution and drying, it was possible to isolate 10.2 g (= 67% of theoretical) of a brown, crystalline substance which, by means of elementary analysis, titration (of the N-O-H group) and spectra, was determined to be N-(2-nitrophenyl)-N-(3-nitro-4-nitrosophenyl)-hydroxylamine; melting point: 130° C.–133° C. (decomposition).

EXAMPLE XXI

Analogous to Example XX, m-nitro-nitrosobenzene was converted with methane sulfonic acid (analogous reaction conditions, same molar quantities, same processing).

It was thereby possible to obtain 11.7 g (= 77% of theoretical) of N-(3-nitrophenyl)-N-(2-nitro-4-nitrosophenyl)-hydroxylamine as a light brown compound; melting point: 135° C.–140° C. (decomposition). Purification was performed by dissolving in 10% soda lye (or 10% $Na_2SO_3$) and precipitating with dilute hydrochloric acid.

EXAMPLE XXII 8.2 g (50 mmol) of 2-nitroso-benzoic acid methyl ester were dissolved in 50 ml of methylene chloride and 7.2 g (75 mmol) of methane solufonic acid added thereto at 0° C. Upon addition of the methane sulfonic acid, the green solution turned dark red. During the entire duration of the reaction the temperature of the reaction mixture did not exceed 10° C. After 1 hour (as described in detail in previous Examples), the solution was sprayed onto water under a vacuum and the methylene chloride removed at the same time. By means of filtration it was possible to obtain 3.6 g (44% of theoretical) of N-(2-carbomethoxyphenyl)-N-(3-carbomethoxy-4-nitrosophenyl)-hydroxylamine in the form of a beige powder (decomposition from 85° C. on), the identity of which was ascertained by means of elementary analysis, titration and spectra (NMR, UV, IR).

An additional part of the compound can be obtained from the red, aqueous-acid filtrate (neutralization and extraction with methylene chloride). The compound can likewise be purified by reprecipitation with Ca-$(OH)_2$ and dilute hydrochloric acid.

EXAMPLE XXIII 5.0 g of 97% p-nitrosotoluene (41.2 mmol) and 4.75 g (44 mmol) of nitrosobenzene were dissolved in 50 ml of methylene chloride at 10° C. Subsequently, 12.7 g (132 mmol) of methane sulfonic acid at 0° C. were added to the mixture within 5 minutes with vigorous stirring.

After completion of the addition, the deep red reaction mixture was stirred for another 10 minutes at room temperature and subsequently sprayed into water of 20° C. under a vacuum, whereby the methylene chloride evaporated and a yellowish brown precipitate appeared at the same time.

After filtration, the product was dissolved in calcium hydroxide solution, freed from some insoluble, tar-like material by filtration and then precipitated by means of the addition of a dilute mineral acid (to pH = 2).

As a result, 7.36 g (= 75% of theoretical) of a yellowish green, mixed product, consisting of N-(4-nitrosophenyl)-N-phenylhydroxylamine and N-(4-tolyl)-N-(4-nitrosophenyl)-hydroxylamine were obtained.

EXAMPLE XXIV

A 1.5 molar solution of nitrosobenzene in methylene chloride of 10° C. and methane sulfonic acid of 5° C. were thoroughly mixed by means of a mixing nozzle, whereby the methane sulfonic acid was metered at such a rate, that a molar ratio of nitrosobenzene:methane sulfonic acid = 1:1.5 came about. The reaction mixture was then pumped into a spiral tube cooled from the outside by means of an ice/salt mixture and with such a length, that, beginning from the joining of the reaction constituents in the mixing nozzle, to the emergence of the reaction product from the spiral tube a total of 45 seconds would elapse. From the reaction coil, the reaction mixture went directly into water at 20° C. under a vacuum, whereby the solvent evaporated and the desired dimer simultaneously accumulated in the form of a yellow powder.

This experimental arrangement was operated continuously and produced a dimer yield of 96%–98%, referred to the nitrosobenzene charge.

What is claimed is:

1. In a process for the preparation of para-nitrosodiphenylhydroxylamines wherein one member selected from the group consisting of nitrosobenzene, ortho-substituted nitrosobenzenes, meta-substituted nitrosobenzenes, ortho-meta-disubstituted nitrosobenzenes, and para-substituted nitrosobenzenes, is reacted with one member selected from the group consisting of nitrosobenzenes, ortho-substituted nitrosobenzenes, meta-substituted nitrosobenzenes, and ortho-meta-disubstituted nitrosobenzenes in the presence of an acid catalyst, the improvement comprising utilizing as the acid catalyst an acid selected from the group consisting of aliphatic, cycloaliphatic, and aromatic sulfonic acids, having a $pK_a$ equal to or less than 1, perchloric acid, and trifluoroacetic acid, in an amount equal to or greater than 0.5 mol of acid per mol of nitroso reactants, and performing the reaction at a temperature from about −20° C. to 60° C.

2. In the process of claim 1, the improvement wherein the acid catalyst is selected from the group consisting of methane, trifluoromethane, ethane, cyclohexane, benzene, and p-toluene sulfonic acid.

3. In the process of claim 1, the improvement wherein the catalyst is used in a quantity from about 0.5 to about 10 mol, per mol of the nitroso reactants.

4. In the process of claim 1, the improvement wherein the catalyst is used in a quantity from about 0.8 to about 2.0 mol, per mol of the nitroso reactants.

5. The process of claim 1, wherein the reaction is carried out in the presence of an organic solvent.

6. The process of claim 5, wherein the organic solvent is selected from the group consisting of aliphatic, cycloaliphatic, or aromatic hydrocarbons.

7. The process of claim 5, wherein the organic solvent is selected from the group consisting of nitromethane, nitrobenzene, methylene chloride, chloroform, 1,2-dichloroethane, 1,1,1-trichloromethane, and 1,1,2,2-tetrachloroethane.

8. The process of claim 1, wherein the ortho-substituted nitrosobenzenes are selected from the group consisting of o-nitrosotoluene, o-chloronitrosobenzene, o-methoxynitrosobenzene, o-nitronitrosobenzene, 2,6-dichloronitrosobenzene, 2,6-dimethylnitrosobenzene, o-methylnitrosobenzene, and 2-nitrosobenzoic acid methylester; the metasubstituted nitrosobenzenes are selected from the group consisting of m-chloronitrosobenzene, m-trifluoromethylnitrosobenzene, m-fluoronitrosobenzene and m-nitronitrosobenzene; and the ortho-meta-substituted nitrosobenzene is 2,5-dichloronitrosobenzene.

* * * * *